US00PP32973P3

(12) United States Plant Patent
Hansen

(10) Patent No.: US PP32,973 P3
(45) Date of Patent: Apr. 13, 2021

(54) *LAGERSTROEMIA* PLANT NAMED 'LAVA JAVA'

(50) Latin Name: ***Lagerstroemia* (L.) hybrid**
Varietal Denomination: Lava Java

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,862

(22) Filed: Jan. 24, 2019

(65) Prior Publication Data

US 2020/0245519 P1 Jul. 30, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05); *A01H 5/02* (2013.01)

(58) Field of Classification Search
USPC ..... Plt./252
CPC ..... A01H 6/00; A01H 5/02
See application file for complete search history.

*Primary Examiner* — Keith O. Robinson

(57) ABSTRACT

The new and distinct crape myrtle plant named *Lagerstroemia* 'Lava Java' has a dense, broadly-spreading, mounded habit, is ground hardy to at least USDA zone 6, has glossy, dark-green foliage with faint marginal wine blush that emerge deep mahogany-colored. The flowers cover the shrub with magenta-rose from shiny reddish buds. The new plant resists leaf spot and powdery mildew and is useful in the landscape as a specimen, en masse, or as a container plant.

1 Drawing Sheet

Botanical classification: *Lagerstroemia* (L.) hybrid.
Variety denomination: 'Lava Java'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. was on Feb. 1, 2018. After that, on Mar. 12, 2018 the claimed plant was sold by Walters Gardens, Inc., who obtained the plant and all information relating thereto, from the inventor. No plants of *Lagerstroemia* 'Lava Java' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Lagerstroemia* plant, commonly known as Crape Myrtle, and hereinafter referred to by the cultivar name 'Lava Java' or the "new plant." 'Lava Java' is grown primarily as an ornamental for landscape use and for use as a potted plant, and is the result of an ongoing breeding program to produce new and improved garden worthy plants for the ornamental market. The new plant was the result of open-pollinated seed collected by the inventor in fall of 2010 in a cultivated landscape in Raleigh, N.C., USA using 'Whit III' U.S. Plant Pat. No. 10,319 (sold under the trademark PINK VELOUR®) as the seed or female parent. The male or pollen parent is unknown, but may have been any one of a number of hybrids or cultivars in the breeding area. The new plant was given the breeder code H10-01-20.

*Lagerstroemia* 'Lava Java' was initially asexually propagated by stem cuttings at a wholesale perennial nursery in Zeeland, Mich., USA in 2012. The resultant plants from successive generations have demonstrated that the new plant has remained stable and true to type in multiple and successive generations of asexual propagation.

SUMMARY OF THE INVENTION

Plants of the new cultivar 'Lava Java' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Lava Java'. Among the characteristics in combination which distinguish 'Lava Java' as a new and distinct cultivar, unique from all other cultivars known to the inventor are:

1. Dense, broadly-spread mounded growth habit;
2. Glossy foliage emerges deep mahogany and matures to dark-green with faint marginal wine blush;
3. Heavily-branched, striated, reddish-brown colored stems;
4. Magenta-rose flowers in dense panicles open on new growth to cover the shrub;
5. Resistance to *Cercospora* leaf spot and *Erisphe* powdery mildew;
6. Ground hardy to at least USDA hardiness zone 6.

The most similar cultivars known to the inventor include: 'Spiced Plum' U.S. Plant Pat. No. 29,478, 'Cool Beans' U.S. Plant Pat. 29,940, 'Sweet Macchiato' U.S. Plant Pat. No.

28,759, and the three copending cultivars 'Brew Ha Ha' U.S. Plant Pat. No. 31,206, 'Dark Roast' U.S. Plant patent application Ser. No. 16/350,861 and 'Chai Berry' U.S. Plant patent application Ser. No. 16/350,860. 'Spiced Plum' is slightly shorter and narrower in habit and blooms with flowers that are more raspberry-purple. 'Cool Beans' has a flower color that is a different pink hue. 'Sweet Macchiato' has a flower color that is more lavender pink coloration. 'Brew Ha Ha' is slightly shorter in habit and the flower color is a different hue of bubblegum pink. 'Dark Roast' is shorter in habit, the leaves are deeper reddish purple and the flowers are a different hue of bright fuchsia pink. 'Chai Berry' is slightly taller in habit and the flowers are a different hue of rose-pink. The female parent 'Whit III' is much taller, the flowers are a pink coloration. Comparison with the male parent is not possible since the male parent is unknown.

BRIEF DESCRIPTION OF THE DRAWINGS

The accompanying color photographs illustrate the flower and foliage characteristics and the overall appearance of a seven-year-old plant of 'Lava Java', growing in a full-sun trial garden in Zeeland, Mich., showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
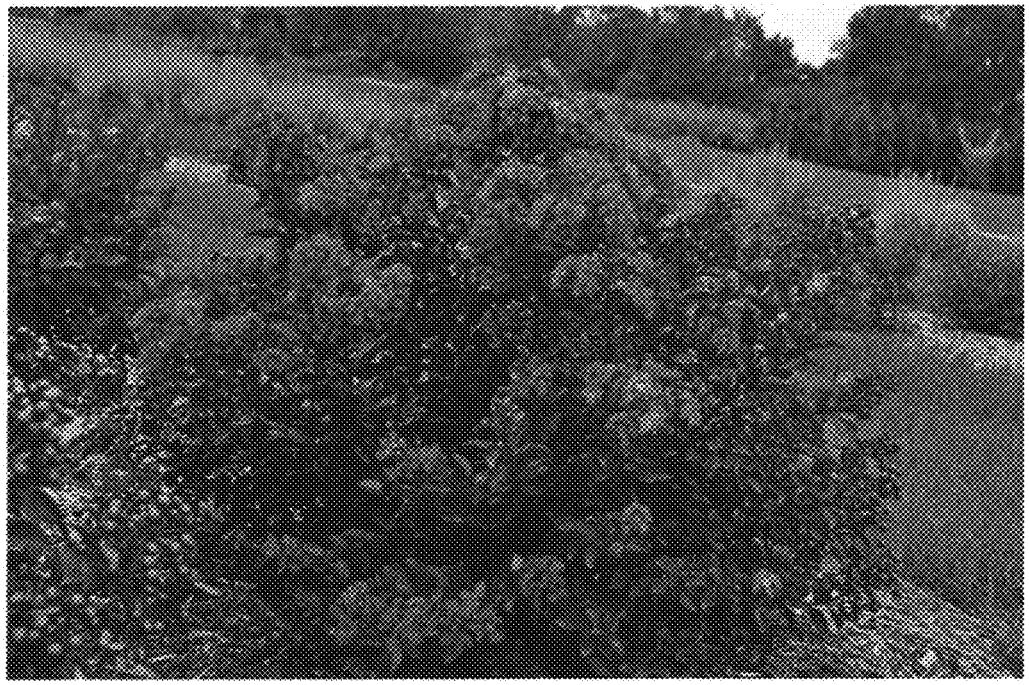
FIG. 1 shows a plant in a full-sun trial garden in late summer peak flowering.
Figure 2:
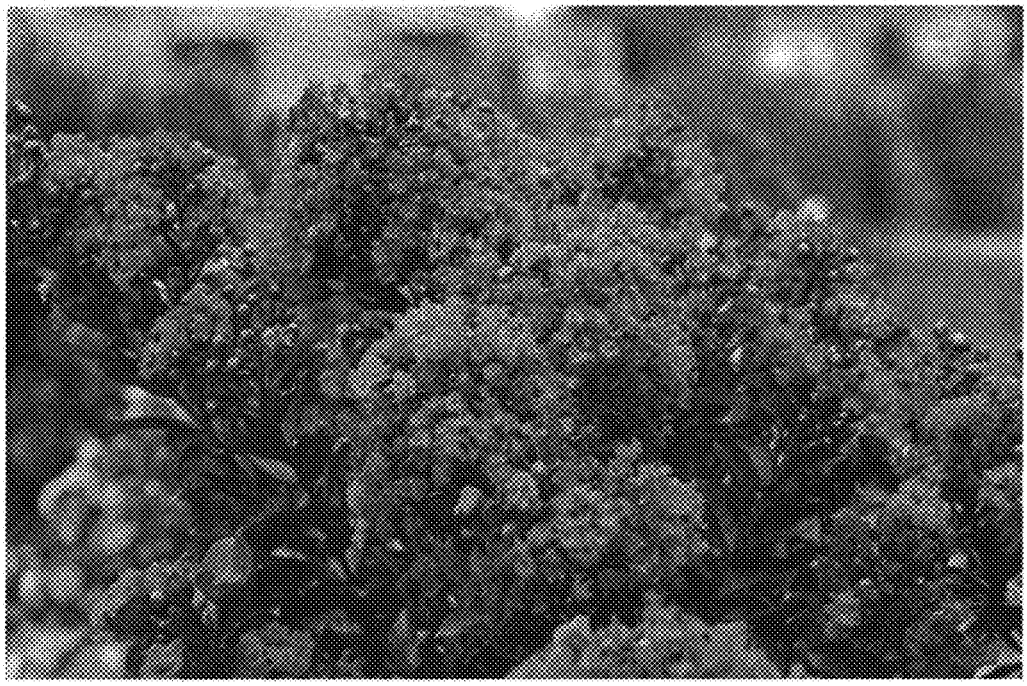
FIG. 2 shows a close-up for the flowers and buds.

The following color references are based on the 2015 edition of The Royal Horticultural Society Colour Chart except where common dictionary terms are used. The following observations and size descriptions are of approximately seven-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* (L.) hybrid; Parentage: female, or seed parent 'Whit III'; the male, or pollen parent is unknown;

Propagation: Terminal softwood stem cuttings;

Time to initiate roots: About three weeks;

Growth rate: Moderate; finishing from a 65 mm liner in a 3.7 liter container in about 10 to 14 weeks in the summer season;

Plant description: Deciduous, woody, narrow, compact flowering shrub; about six mainly upright to outward primary stems; freely branched;

Root description: Fine, numerous, fibrous, well-branched;

Plant habit: Broadly-spreading compact mound; about 115.0 cm high from the soil level to the top of the inflorescences; about 102.0 cm wide with no pinching, pruning or plant growth regulators;

Stems: About sixteen; to about 80.0 cm long and about 20.0 mm diameter at base; young stems cylindrical with four longitudinal carinae, along line on either side of petioles; basal stems cylindrical with slightly exfoliating bark; highly branched with about 18 to 23 alternate branches held at about 30 to 45 degree angle above horizontal; branches to about 35.0 cm long and 5.0 mm diameter at base;

Stem color: Woody basal portion variable with over wintered stems between RHS 177B and RHS 200A, basal new season stems striated with nearest RHS 176A and RHS 164D; young developing stems striated with nearest RHS 181C and nearest RHS 185A;

Node: About 35 to 45 per main stem; internode length average about 1.5 cm in main stems;

Node color: Same as surrounding stem;

Foliage description: Sub-opposite to alternate; simple; ovate; margin ciliolate; slightly coarsely sinuate; acute apex; aequilateral, rounded to attenuate base; adaxial and abaxial glabrous and lustrous; to about 7.6 cm long and 3.4 cm wide, average about 5.5 cm long and 3.4 cm wide;

Abaxial leaf color: Young emerging adaxial nearest RHS 187A with slight marginal blush of nearest RHS 187B, abaxial nearest RHS 146D; mature adaxial nearest RHS 139A, abaxial between RHS 137B and RHS 146B;

Veins: Pinnate, micro-puberulent adaxial and abaxial;

Vein color: Young emerging adaxial nearest RHS N186C, abaxial between RHS 183C and RHS 187C; mature adaxial nearest RHS 183C with midrib nearest RHS NN137C in distal portion, abaxial basal midrib with distal midrib portion and secondary veins nearest RHS 160B with blush of nearest RHS 184A;

Petiole: Short, typically 2.0 mm long and 2.0 mm wide; color adaxial center nearest RHS 146A and margins nearest RHS N187A abaxial nearest RHS N187A;

Inflorescence: Panicle; terminal branched panicles up to about 400 flowers; average about 275 flowers; up to about 35.0 cm long and about 25.0 cm across; beginning late-summer and continuing for up to nine weeks;

Buds: Globose; slightly carinate; with rounded to slightly apiculate apex and rounded base; lustrous; glabrous; about 7.5 mm long and about 8.0 mm diameter one day prior to opening; longitudinal suture lines of medium prominence;

Bud color: Exposed petals nearest RHS 64A; calyx nearest RHS 183C with carinae nearest RHS 187A;

Flowers: Perfect; regular; actinomorphic; in terminal panicle; individually about 2.8 cm across and about 20.0 mm long to tip of exserted stigma, corolla to about 18.0 mm long; lasting about is two days;

Flower fragrance: Faintly sweet;

Peduncle: Cylindrical with four longitudinal carinae in proximal portion and cylindrical in distal portion; about 5.0 mm diameter at base below lowest flowering branch, to about 35.0 cm long and 18.0 cm across;

Peduncle color: Variable with position; proximal between RHS 177B and RHS 200A, and distal portion striated with nearest RHS 181C and nearest RHS 185A;

Pedicel: Cylindrical; glabrous; lustrous; about 9.0 mm long and 1.0 mm diameter;

Pedicel color: Nearest RHS 187A;

Calyx: Fused to form hypanthium; 9.0 mm long and 7.0 mm across;

Sepals: Fused in about the basal 3.0 mm; acute apex, entire margin; glabrous and lustrous both adaxial and abaxial; about 7.0 mm long and individually and about 3.0 mm wide at fusion point;

Sepal color: Adaxial basal portion nearest RHS 196D, middle portion nearest RHS 187C, distal portion nearest RHS N148D; abaxial basal nearest RHS 183C;

Petals: Six; stalked; glabrous; blade ruffled or crisped; margin crisped; blade with rounded apex and auriculate base, to about 10.0 mm across and 10.0 mm long; claw base or stalk adnate to calyx, to about 8.0 mm long and 0.7 mm diameter; overall about 18.0 mm long;

Petal color: Blade adaxial and abaxial nearest RHS 60A; claw nearest RHS 53B;

Androecium:

*Stamens*.—Typically about 42; six longer and about 36 shorter.

*Filaments*.—Cylindrical; shorter stamens to about 10.0 mm long and about 0.2 mm diameter, curved to twisted; longer filaments about 18.0 mm long and about 0.3 mm diameter; color of shorter filaments nearest RHS 179C; color longer filaments nearest RHS 60B.

*Anthers*—Dorsifixed; flattened ellipsoid; more developed on longer stamens to about 1.5 mm long and 1.2 mm across, on shorter stamens about 1.0 mm long and about 0.7 mm across; color nearest RHS 13A.

*Pollen*.—Abundant on longer stamens; color nearest RHS 14A.

Gynoecium: One; about 20.0 mm long;

*Style*.—Cylindrical; glabrous; about 18.0 mm long and 1.0 mm diameter; color nearest RHS 53B.

*Stigma*.—Globose; about 0.7 mm diameter; color nearest RHS 59A.

*Ovary*.—Superior; globose; lustrous; about 2.0 mm tall and 2.5 mm diameter; color nearest RHS 150D.

Fruit: Globose; dehiscent, loculicidal, penta-valved capsule; about 9.0 mm across and 9.0 mm tall; immature color nearest RHS 145C, mature color nearest RES 202B with midribs nearest RHS 165A;

Seed: Typically 15 to 30 seeds per fruit; winged; to about 7.0 mm long and 15 mm across and 1.0 mm thick at embryo; color variable, nearest RHS 199B at embryo and RHS 161C in wing;

Disease resistance: *Lagerstroemia* 'Lava Java' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named *Lagerstroemia* 'Lava Java' essentially as herein illustrated and described.

* * * * *